US009572821B2

(12) United States Patent
Skulachev et al.

(10) Patent No.: US 9,572,821 B2
(45) Date of Patent: Feb. 21, 2017

(54) PHARMACEUTICAL COMPOSITIONS FOR PREVENTING AND TREATING EYE PATHOLOGIES

(71) Applicant: MITOTECH SA, Luxembourg (LU)

(72) Inventors: Vladimir P. Skulachev, Moscow (RU); Maxim V. Skulachev, Moscow (RU)

(73) Assignee: MITOTECH SA, Luxembourg (LU)

( * ) Notice: Subject to any disclaimer, the term of this patent is extended or adjusted under 35 U.S.C. 154(b) by 0 days.

(21) Appl. No.: 14/163,193

(22) Filed: Jan. 24, 2014

(65) Prior Publication Data
US 2014/0142066 A1 May 22, 2014

Related U.S. Application Data

(62) Division of application No. 12/445,897, filed as application No. PCT/RU2006/000546 on Oct. 20, 2006, now Pat. No. 8,658,624.

(51) Int. Cl.
A61K 31/66 (2006.01)
A61K 31/122 (2006.01)

(52) U.S. Cl.
CPC ............. *A61K 31/66* (2013.01); *A61K 31/122* (2013.01)

(58) Field of Classification Search
CPC .......................... A61K 31/66; A61K 31/122
See application file for complete search history.

(56) References Cited

U.S. PATENT DOCUMENTS

| | | | |
|---|---|---|---|
| 5,538,974 | A | 7/1996 | Ogawa et al. |
| 6,331,532 | B1 | 12/2001 | Murphy et al. |
| 7,109,189 | B2 | 9/2006 | Murphy et al. |
| 2002/0044913 | A1 | 4/2002 | Hamilton |
| 2005/0065099 | A1 | 3/2005 | Walkinshaw et al. |

FOREIGN PATENT DOCUMENTS

| | | |
|---|---|---|
| EP | 1047701 B1 | 5/2005 |
| EP | 1534720 A1 | 6/2005 |
| EP | 1321138 B1 | 4/2006 |
| WO | 99/26582 A2 | 6/1999 |
| WO | 2004/014927 A1 | 2/2004 |
| WO | 2006/005759 A2 | 1/2006 |

OTHER PUBLICATIONS

Viana et al. (2004) "Hypoglycemic and anti-lipemic effects of the aqueous extract from Cissus sicyoides," BMC Pharmacol. 4:9 (7 pages).
Villa et al. (2004) "Animal models of endotoxic shock" Meth. Mol. Med., 98:199-206.
Vollset et al. (2000) "Plasma total homocysteine, pregnancy complications, and adverse pregnancy outcomes: the Hordaland Homocysteine study," Am. J. Clin. Nutr., 71:962-968.
Weyer et al. (1999) "Development of beta3-adrenoceptor agonists for the treatment of obesity and diabetes—an update," Diabetes Metab., 25:11-21.
Zamzami et al. (1996) Mitochondrial control of nuclear apoptosis. J Exp Med 183, 1533-1544.
Zoratti et al. (1995). "The mitochondrial permeability transition." Biochim. Biophys. Acta 1241:139-176.
Zettl et al. (2005) "Investigation of micelle formation by fluorescence correlation spectroscopy," J. Phys. Chem. B. 109:13397-13401.
Zorov et al. (2000) Reactive oxygen species (ROS)-induced ROS release: a new phenomenon accompanying induction of the mitochondrial permeability transition in cardiac myocytes. J Exp Med 192(7), 1001-1014.
Zorov et al. (2006). Mitochondrial ROS-induced ROS release: an update and review. Biochim Biophys Acta 1757, 509-517.
International Search Report and Written Opinion of the International Searching Authority, PCT/US12/40711, Aug. 20, 2012 (9 pages).
Jolkkonen (2000), "Behavioral effects of the alpha(2)-adrenoceptor antagonist, atipamezole, after focal cerebral ischemia in rats," Eur. J. Pharmacol., 400:211-219.
Juhaszova et al. (2004), "Glycogen synthase kinase-3beta mediates convergence of protection signaling to inhibit the mitochondrial permeability transition pore," J. Clin. Invest. 113:1535-1549.
Adlam et al. (2005) "Targeting an antioxidant to mitochondria decreases cardiac ischemia-reperfusion injury," FASEB J. 19:1088-1095.
Havens, et al. (2006) "Regulation of Late G1/S Phase Transition and APCCdh1 by Reactive Oxygen Species," Mol. Cell. Biol. 26(12):4701-4711.
Sundaresan, et al. (1995) "Requirement for Generation of H2O2 for Platelet-Derived Growth Factor Signal Transduction," Science, 270:296-299.
Becker (2004) "New concepts in reactive oxygen species and cardiovascular reperfusion physiology" Cardiovasc. Res. 61:461-470.
Berge et al. (1977) "Pharmaceutical Salts," J. Pharma. Sci., 66(1):1-19.
Blaikie et al. (2006) "Targeting Dinitrophenol to Mitochondria: Limitations to the Development of a Self-limiting Mitochondrial Protonophore," Biosci. Rep., 26:231-243.
Brand et al. (1992) "The mechanism of the increase in mitochondrial proton permeability induced by thyroid hormones," Eur. J. Biochem. 206:775-781.
13-Methoxydihydronitidine—Compound Summary PubChem compound CID 38845; Mar. 26, 2005 (Mar. 26, 2005) [retrieved__ from http://pubchem.ncbi.nlm.nih.gov/summary/summary. cgi?cid=38845&loc=ec__rcs on Jul. 31, 2012] whole doc (4 pages).
Emiko et al. "Manganese Superoxide Dismutase protects against oxidation-induced apoptosis in mouse retinal pigment epithelium: implications for age-related macular degeneration," Invest. Ophthalmol. Vis. Sci., 46(9): 3426-3434.
Green et al. (2004) "Prevention of Mitochondrial Oxidative Damage as a Therapeutic Strategy in Diabetes," Diabetes, 53(1):S110-S118.
Hansford et al. (1997) "Dependence of H2O2 formation by rat heart mitochondria on substrate availability and donor age," J. Bioenerg. Biomem. 29(1):89-95.

(Continued)

*Primary Examiner* — Zohreh Fay
(74) *Attorney, Agent, or Firm* — Ann-Louise Kerner, J.D.; DLA Piper LLP (US)

(57) ABSTRACT

The present invention relates to pharmacology, medicine, ophthalmology, and, in particular, concerns a class of chemical compounds of structure (I) and also their solvates, isomers or prodrugs applicable when incorporated into pharmaceutical compositions also containing pharmaceutically acceptable carrier which can be useful for prophylaxis and treatment of different eye pathologies such as cataract and macular dystrophy.

7 Claims, 4 Drawing Sheets

(56) References Cited

OTHER PUBLICATIONS

Holloszy (1998) "Longevity of exercising male rats: effect of an antioxidant supplemented diet," Mechanisms of Ageing and Development, 100:211-219.

King et al. (2004) "Mitochondria-derived reactive oxygen species mediate blue light-induced death of retinal pigment epithelial cells," Photochem. Photobiol., 79(5):470-475.

Kirschner et al. (1994) "Role of iron and oxygen-derived free radicals in ischemia-reperfusion injury," J. Am. Coll. Surg., 179:103-117.

Li et al. (2000) "Skeletal muscle respiratory uncoupling prevents diet-induced obesity and insulin resistance in mice," Nat. Med. 6(10):1115-1120.

Liu et al. (1993) "Age-associated changes in superoxide dismutase activity, thiobarbituric acid reactivity and reduced glutathione level in the brain and liver in senescence accelerated mice (SAM): a comparison with ddY mice," Mech. Ageing Dev., 71:23-30.

Longo et al. (2005) "Programmed and altruistic ageing," Nature Reviews Genetics, 6:866-872.

Astrup et al. (1996) "Low resting metabolic rate in subjects predisposed to obesity: a role for thyroid status 1-3," Am. J. Clin. Nutr. 63:879-883.

Mecocci et al. (2000) "Plasma antioxidants and longevity: a study on healthy centenarians," Free Rad. Biol. & Med., 28(8):1243-1248.

Bacsi et al. (2005) "Effect of pollen-mediated oxidative stress on immediate hypersensitivity reactions and late-phase inflammation in allergic conjunctivitis," J. Allergy Clin. Immunol., 116(4): 836-843.

Orr et al. (2003) "Effects of overexpression of copper-zinc and manganese superoxide dismutases, catalase, and thioredoxin reductase genes on longevity in *Drosophila melanogaster*," J. Biol. Chem., 278(29):26418-26422.

Papp et al. (1999) "Glutathione status in retinopathy of prematurity," Free Radic. Biol. & Med., 27(7-8):738-743.

Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.

Petrosillo et al. (2006) "Protective effect of melatonin against mitochondrial dysfunction associated with cardiac ischemia-reperfusion: role of cardiolipin," FASEB J., 20:269-276.

Popova et al. (2006) "MitoQ induced miofibroblast differentiation of human fibroblasts," Biochimica et Biophysica Acta, P2.2. 27:S:433-434.

Pozniakovsky et al. (2005) "Role of mitochondria in the pheromone- and amiodarone-induced programmed death of yeast," J. Cell Biol., 168(2):257-69.

Reddy (2006) "Mitochondrial oxidative damage in aging and Alzheimer's disease: implications for mitochondrially targeted antioxidant therapeutics," J. Biomed. & Biotech., Art. ID 31372:1-13.

Barclay et al. (2003) Phenols as antioxidants, In the Chemistry of Phenols, Part 2, Rappoport, Z., Ed., Wiley, pp. 875 (3 pages).

Riess et al. (2004) "Reduced reactive O2 species formation and preserved mitochondrial NADH and [Ca2+] levels during short-term 17° C. ischemia in intact hearts," Cardiovasc. Res., 61:580-590.

Bernard et al. (2002) "Hytopthermia after cardiac arrest study group. Mild therapeutic hypothermia to improve the neurologic outcome after cardiac arrest," New Engl. J. Med. 346(8):549-556.

Sheu et al. (2006) "Targeting antioxidants to mitochondria: a new therapeutic direction," Biochimica et Biophysica Acta, 1762:256-265.

Sidorova et al. (2004) "Transcriptional activation of cytochrome P450 1A1 with alpha-tocopherol," Bull. Exp. Bio. Med., 138(3):233-236.

Skulachev (2005) "Critical Review: How to Clean the Dirtiest Place in the Cell: Cationic Antioxidants as Intramitochondrial ROS Scavengers," IUBMB Life, 57(4/5):305-310.

Skulachev (2003) "Aging and the programmed death phenomena," Topics in Current Genetics, vol. 3, Nystrom and Osiewacz, Eds., Model Systems in Aging, Springer-Verlag Berlin Heidelberg 191-238.

Starkov et al. (1997) "6-ketocholestanol is a recoupler for mitochondria, chromatophores and cytochrome oxidase proteoliposomes," Biochim. Biophys. Acta. 1318:159-172.

Tompkins et al. (2006) "Mitochondrial dysfunction in cardiac ischemia-reperfusion injury: ROS from complex I, without inhibition," Biochim. Biophys. Acta. 1762:223-231.

Yildirim et al. (2005) "Role of oxidative stress enzymes in open-angle glaucoma," Eye, 19:580-583.

Zweier et al. (1987) "Direct measurement of free radical generation following reperfusion of ischemic myocardium," PNAS USA, 84:1404-1407.

International Search Report dated Dec. 20, 2007 and International Preliminary Report on Patentability dated Nov. 10, 2009, PCT/RU2007/000171, 16 pages.

International Search Report and Written Opinion of the International Searching Authority, PCT/RU2007/000355, Mar. 27, 2008, 10 pages.

PCT International Preliminary Report on Patentability for International Application No. PCT/RU2007/000043, issued Aug. 4, 2009, 7 pages.

Bray et al. (1999) "Sibutramine produces dose-related weight loss," Obes. Res. 7(2):189-198.

Byrom (1933) "Nature of myxoedema," Clin. Sci. 1:273-285.

Cherubini et al. (2005), "Potential markers of oxidative stress in stroke," Free Radic. Biol. Med. 39:841-852.

Clapham et al. (2000) "Mice overexpressing human uncoupling protein-3 in skeletal muscle are hyperphagic and lean," Nature, 406:415-418.

Collins et al. (2004) "Heart protection study collaborative group. Effects of cholesterol-lowering with simvastatin on stroke and other major vascular events in 20536 people with cerebrovascular disease or other high-risk conditions," Lancet 363(9411):757-767.

Coulter et al. (2000) "Mitochondrially targeted antioxidants and thiol reagents," Free Rad. Biol. Med. 28 (10):1547-1554.

Demougeot et al. (2004) "Cytoprotective efficacy and mechanisms of the liposoluble iron chelator 2,2'-dipyridyl in the rat photothrombotic ischemic stroke model," J. Pharmacol. Exper. Ther. 311:1080-1087.

Denisov (2006) "Reactivity of quinones as alkyl radical acceptors," Kinetics and Catalysis, 45(5):662-671.

Dominguez (2006) "Ageing, lifestyle modifications, and cardiovascular disease in developing countries," J. Nutr. Health Aging, 10(2):143-149.

Smith, et al. (2003) "Delivery of bioactive molecules to mitochondria in vivo," PNAS, 100(9):5407-5412.

Karl et al. (2003) "Behavioral phenotyping of mice in pharmacological and toxicological research," Exp. Toxicol. Pathol., 55(1):69-83.

Kasahara, et al. (2005) "Manganese Superoxide Dismutase protects against oxidation-induced apoptosis in mouse retinal pigment epithelium: implications for age-related macular degeneration," Author Manuscript, NIH Public Access PMC Nov. 1, 2005 : 1-18, Invest. Ophthalmol. Vis. Sci., 46(9):3426-3434.

Kirkinezos et al (2001) "Reactive Oxygen species and Mitochondrial Diseases," Seminars in Cell & Developmental Biology, 12:449-457.

Kirste et al. (1995) "Continuous-wave electron spin resonance studies of porphyrin and porphyrin-quinone triplet states," J. Chem. Soc. Perkin Trans. 2:2147-2152.

Kroemer et al. (1995). The biochemistry of programmed cell death. FASEB J., 9:1277-1287.

Kromhout (2001) "Diet and cardiovascular diseases," J. Nutr. Health Aging, 5:144-149.

Kurreck et al. (1995) "Mimicking primary processes in photosynthesis covalently linked porphyrin quinones," Radiation Physics and Chemistry, 45(6):853-865.

Kutala et al. (2006) "Prevention of postischemic myocardial reperfusion injury by the combined treatment of NCX-4016 and Tempol." J. Cardiovasc. Pharmacol., 48(3):79-87.

(56) References Cited

OTHER PUBLICATIONS

Li et al. (2002) "Activation of macrophage nuclear factor-kappa B and induction of inducible nitric oxide synthase by LPS," Respir. Res., 3:23 (6 pages).

Liu et al. (1996), "Induction of apoptotic program in cell-free extracts: requirement for dATP and cytochrome c," Cell 86:147-157.

Lysenko et al. (2001) "Thrombocytopathies and their role in the development of hemorrhagic syndrome in vascular diseases of the fundus oculi," Vestn. Oftalmol., 117(1):24-26 (English Translation of Russian article abstract—1 page).

Maire et al. (2001) "Factors associated with hyperhomocysteinemia in Crohn's disease," Gastroenterol. Clin. Biol., 25 (8-9):745-748 (French-abstract only, 1 page).

Malenka et al. (1999) "Long-term potentiation: a decade of progress?" Science, 285(5435):1870-1874.

Matsumoto et al. (1992), "Antioxidant effect on renal scarring following infection of mannose-sensitive-piliated bacteria," Nephron. 60:210-215.

Monaco et al. (2004) "Canonical pathway of nuclear factor kB activation selectively regulates proinflammatory and prothrombotic responses in human atherosclerosis," PNAS, 101(15):5634-5639.

Mundi et al. (1991), Extracellular release of reactive oxygen species from human neutrophils upon interaction with *Escherichia coli* strains causing renal scarring, Infect. Immun. 59(11):4168-4172.

Murphy (1997), "Selective Targeting of Bioactive Compounds to Mitochondria," Trends in Biotechnology, 15 (8):326-330.

Oddo et al. (2003) "Triple-transgenic model of Alzheimer's disease with plaques and tangles: intracellular Abeta and synaptic dysfunction," Neuron, 39:409-421.

O'Hanley et al. (1996), "Prospects for urinary tract infection vaccines. In: Urinary Tract Infections: Molecular Pathogenesis and Clinical Management," (Mobley, H. L. T. & Warren, J.W., eds), (Washington, DC: ASM Press), pp. 405-425 (23 pages).

O'Hanley et al. (1991), "Alpha-hemolysin contributes to the pathogenicity of piliated digalactoside-binding *Escherichia coli* in the kidney: efficacy of an alpha-hemolysin vaccine in preventing renal injury in the BALB/c mouse model of pyelonephritis," Infect. Immun. 59(3):1153-1161.

Okada et al. (2005) "The implications of the upregulation of ICAM-1/VCAM-1 expression of corneal fibroblasts on the pathogenesis of allergic keratopathy," Invest. Ophthalmol. Vis. Sci., 46(12):4512-4518.

Parascandola (1974), "Dinitrophenol and bioenergetics: an historical perspective," Mol. Cell. Biochem., 5(1-2):69-77.

Petit-Demouliere et al. (2005), "Forced swimming test in mice: a review of antidepressant activity," Psychopharmacol., 177:245-255.

Poehlman et al. (1989), "A review: exercise and its influence on resting energy metabolism in man," Med. Sci. Sports Exerc., 21(4):515-525.

Rodriguez-Spong et al. (2004), "General Principles of Pharmaceutical Solid Polymorphism: A Supramolecular Perspective," Advanced Drug Delivery Reviews, 56:241-274.

Saifer et al. (1957), "Laboratory Methods: The photometric microdetermination of blood glucose with glucose oxidase," J. Lab. Clin. Med., 51(3):448-460.

Sarter (2002), Coenzyme Q10 and Cardiovascular Disease: A Review, J. Cardiovasc. Nurs. 16(4):9-20.

Selkoe (2002), "Alzheimer's disease is a synaptic failure," Science 298:789-791.

Faa et al. (1999), "Iron chelating agents in clinical practice," Coordination Chemistry Reviews, 184(1):291-310.

Galkina et al. (2004), "Endothelium-leukocyte interactions under the influence of the superoxide-nitrogen monoxide system," Med. Sci. Monit., 10:BR307-316.

Skulachev (2005), "Critical Review: How to Clean the Dirtiest Place in the Cell: Cationic Antioxidants as Intramitochondrial ROS Scavengers," IUBMB Life, 57(4/5):305-310.

Green (1974), "The electromechanochemical model for energy coupling in mitochondria," Biochimica et Biophysica Acta, 346:27-78.

Gear (1974), "Rhodamine 6G: A potent inhibitor of mitochondrial oxidative phosphorylation," J. Biol. Chem., 249 (11):3628-3637.

Giamarellos-Bourboulis et al. (2006), "Oleuropein: a novel immunomodulator conferring prolonged survival in experimental sepsis by Pseudomonas aeruginosa," Shock, 26(4):410-416.

Giorgini et al. (2001), "Reactivity of ubiquinones and ubiquinols with free radicals," Free Rad. Res., 35:63-72.

Goldstein (2002), "Reactive oxygen species as essential components of ambient air," Biochemistry (Mosc.) 67:161-170.

Gong et al. (1997), "Uncoupling protein-3 is a mediator of thermogenesis regulated by thyroid hormone, beta3-adrenergic agonists, and leptin," J. Biol. Chem., 272(39):24129-24132.

Skulachev et al. (2005), "Aging as mitochondria-mediated atavistic program. Can aging be switched off?" Ann. N.Y. Acad. Sci., 1057:145-164.

Griffiths et al. (2001), "Genetic analysis of collagen-induced arthritis in rats: a polygenic model for rheumatoid arthritis predicts a common framework of cross-species inflammatory/autoimmune disease loci." Immunol. Rev. 184:172-83.

Spector (1995), "Oxidative stress-induced cataract: mechanism of action," FASEB J., 9:1173-1182.

Spencer et al. (1998), "Transition metal chelators reduce directly measured myocardial free radical production during reperfusion," J. Cardiovasc. Pharmacol., 32(3):343-348.

Triet et al. (1993), "Anxiogenic stimuli in the elevated plus-maze," Pharmacol. Biochem. & Behav. 44:463-469.

Hess et al. (2002), "Biological and Chemical Applications of Fluorescence Correlation Spectroscopy: A Review," Biochem. 41(3):697-705.

Hummel et al. (1966) "Diabetes, new mutation in the mouse." Science, 153:1127-1128.

Hunter et al. (1979), "The Ca2+-induced membrane transition in mitochondria. I. The protective mechanisms," Arch. Biochem. Biophys., 195:453-459.

Hvizdos et al. (1999) "Orlistat: a review of its use in the management of obesity," Drugs, 58(4):743-760.

Johnson et al. (1980) "Localization of Mitochondria in Living Cells with Rhodamine 123," Proc. Natl. Acad. Sci. USA, 77(2):990-994.

USDH (2005) "Guidance for Industry: Estimating the Maximum Safe Starting Dose in Initial Clinical Trials for Therapeutics in Adult Healthy Volunteers," U.S. Dept. of Health and Human Services, FDA, CDER, 30 pages.

Vanden Hoek et al. (1996) "Reperfusion injury in cardiac myocytes after simulated ischemia," Am. J. Phys., 270:1334-1341.

ature of the United States Patent

PHARMACEUTICAL COMPOSITIONS FOR PREVENTING AND TREATING EYE PATHOLOGIES

CROSS-REFERENCE TO RELATED APPLICATIONS

This application is a divisional of U.S. application Ser. No. 12/445,897, entitled "Pharmaceutical Compositions for Preventing and Treating Eye Pathologies," which was filed Aug. 31, 2010, which is a national stage entry of PCT/RU06/00546, filed on Oct. 20, 2006. The entirety of the aforementioned applications is herein incorporated by reference.

FIELD OF THE INVENTION

This invention relates to pharmacology, medicine, ophthalmology, and, in particular, concerns a class of chemical compounds of structure (I) which being incorporated into pharmaceutical compositions can be used for prophylaxis and treatment of different eye pathologies such as cataract and macular dystrophy.

BACKGROUND

At present, various methods of treatment of eye pathologies—surgical and medicamental, are applied in medical practice. Medicamental methods usually comprise natural and synthetic compounds possessing antioxidant properties (antioxidants).

In pathogenesis of many eye pathologies (including cataract and macular dystrophy), the oxidative stress—disruption of the balance between production of free radicals and their elimination by antioxidants, plays an important role.

Only bioactive nutrients containing natural carotenoids possessing antioxidant properties—lutein and zeaxanthin have been available in Russia to date. Said compounds also contain plant carotenoid beta-carotene (1.5 mg) that plays an important role in the formation of a visual pigment rhodopsin providing an eye with adaptation to the lowered lighting; antioxidants—vitamins E and C, micronutrients zinc and copper which are also important to maintain the health of eyes.

Age-related macular degeneration (AMD) occupies a highly important place in the world among disorders leading to persistent deterioration of visual functions and blindness (J. Evans, C. Rooney, F. Ashood, 1996). AMD is one of the eye diseases which are difficult to treat (L. N. Marchenko, 2001). The Russian Central Scientific Research Institute of Expertise of Work Capability and Organization of Labor of the Disabled reported in 1997 that the vascular diseases of retina resulting in eye disability in particular comprise nonexudative age-related macular degeneration—39.4%, exudative age-related macular degeneration—9.1%, bloodstream disruption in great retina vessels—51.5%. Age-related macular degeneration constituted about 10% of blindness registered in the Western Europe 25 years ago, this value has increased up to 50% to date (V. S. Akopyan, 2004). According to the reports of WHO/OMS (1986), increase in proportion of elders within the human population leads to annual increase in said disease. The history of macular degeneration problem originated from 1855 when F. S. Donders described macular drusen. The term "senile macular degeneration" was first introduced by O. Haab in 1885. Later on, C. Behr (1920) and H. F. Falls (1949) assigned said pathology to hereditary familial diseases. Taking into account a variety of clinical and ophthalmoscopic data, different terms have been applied to age-related macular degeneration in the literature. To date a consensus exists among ophthalmologists that all these pathology types are a manifestation of the same disease that now is often designated in the literature as "age-related macular degeneration" (AMD).

AMD is a pathology of central photoactive area of retina. The disease is a chronic dystrophic process when choriocapillaries, Bruch's membrane and pigment retinal epithelium are predominantly affected followed by the affection of photoreceptors (Lysenko et al. (2001). The extent of the process severity and the loss of central vision depends on AMD type and vicinity of dystrophic process to central fossa of retina. AMD is most commonly double-sided process. The second eye was observed to be affected within 5 years after the affection of the first eye (H. C. Zweng, 1977).

Progression of macular degeneration results in increased light sensitivity, eyesight degradation, gradual loss of eyeshots, and finally appearance of turbid spot in the center of visual field (relative or absolute scotoma). The reasons resulting in macular degeneration are different. However the role of genetic factors and damaging action of light are undoubted. At present, the consequences of negative effect of free oxygen radicals are often discussed in the scientific literature. Photochemical reaction induced by light and oxygen results in the formation of highly reactive free radicals which are capable for damaging light sensitive cells of eye retina. The older is a person, the more dangerous is the effect of free radicals—natural aging correlates with decline of the activity of intrinsic protective antioxidant system of an organism that accelerates dystrophic processes.

Prolonged computer work also leads to eyesight degradation. Computer monitor is a source of serious hazard to eyes since it radiates ultraviolet light, the effect of the latter is enhanced when luminescent lamps are used. Coupled with hard work of eyes, this can cause fast exhaustion, headaches, decrease in capability for work, eye pain, lachrymation. According to statistics, from 50% to 90% of persons engaged in computer working have such complaints when see a doctor. These complaints are combined into the term "computer vision syndrome". To increase antioxidant protection of eyes, persons engaged in computer working need additional administration of antioxidants.

Vitamins-antioxidants such as vitamins C and E, bioflavonoids, beta-carotene also protect eyes from damaging and facilitate anabolic processes supporting collagen biosynthesis. Combined administration of N-acetyl-cysteine, lipoic acid and vitamins C and E stimulates biosynthesis of antioxidant enzymes of eye tissue, glutathione.

DESCRIPTION

One of the aspects of the present invention is a pharmaceutical composition for prophylaxis and treatment of different eye pathologies comprising a compound that includes targeting moiety, linker group and antioxidant. In general, such a compound can be described by the following structure (I):

(structure I)

wherein A is an effector—antioxidant of structure:

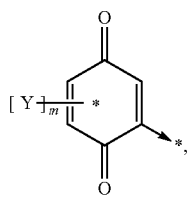

and/or reduced form thereof, wherein m is an integer from 1 to 3; each Y is independently selected from the group consisting of: lower alkyl, lower alkoxy; or two adjacent Y groups, together with carbon atoms to which they are attached form the following structure:

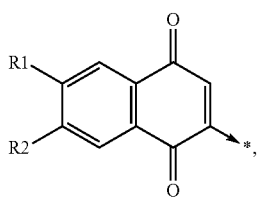

and/or reduced form thereof, wherein R1 and R2 may be the same or different and are each independently lower alkyl or lower alkoxy;

L is a linker group, comprising:
a) straight or branched hydrocarbon chain optionally substituted with one or more substituents and optionally containing one or more double or triple bonds; or
b) natural isoprene chain; and
n is integer from 1 to 20;
B comprises:
a) a Skulachev-ion Sk:

Sk⁺Z⁻ where Sk is a lipophilic cation, and Z is a pharmacologically acceptable anion; and/or
b) a charged hydrophobic peptide containing 1-20 amino acid residues;
with proviso that in compound of structure (I) A is neither ubiquinone (e.g. 2-methyl-4,5-dimethoxy-3,6-dioxo-1,4-cyclohexadienyl) nor tocopherol or a mimetic of superoxide dismutase or ebselen; when L is neither divalent decyl nor divalent pentyl nor divalent propyl radical; and when B is triphenylphosphonium cation; including solvates, isomers or prodrugs thereof.

A further aspect of the present invention is a pharmaceutical composition for prophylaxis and treatment of different eye pathologies comprising a compound of structure (I), wherein A is a plastoquinone of structure:

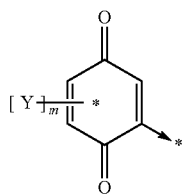

wherein Y is methyl, m=2;
L is a linker group, comprising:
a) straight or branched hydrocarbon chain optionally substituted with one or more substituents and optionally containing one or more double or triple bonds; or
b) natural isoprene chain;
n is integer from 1 to 20;
B comprises:
a) a Skulachev-ion Sk:

Sk⁺Z⁻ where Sk is a lipophilic cation, and Z is a pharmacologically acceptable anion; and/or
b) a charged hydrophobic peptide containing 1-20 amino acid residues;
with proviso that in compound of structure (I) A is neither ubiquinone (e.g. 2-methyl-4,5-dimethoxy-3,6-dioxo-1,4-cyclohexadienyl) nor tocopherol nor mimetic of superoxide dismutase or ebselen; when L is neither divalent decyl nor divalent pentyl nor divalent propyl radical; and when B is triphenylphosphonium cation; including solvates, isomers or prodrugs thereof.

A further aspect of the present invention is a pharmaceutical composition for prophylaxis and treatment of different eye pathologies comprising a compound of structure (I)—SkQ1:

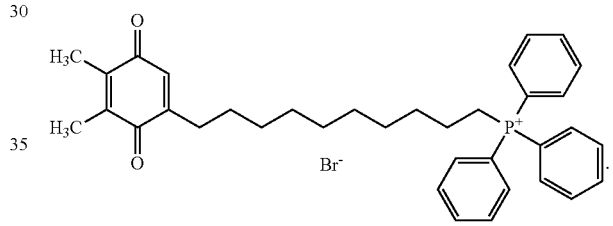

SkQ1 (3)

A further aspect of the present invention is a pharmaceutical composition for prophylaxis and treatment of different eye pathologies comprising therapeutically or prophylactically justified amount of a compound of Structure (I) and at least one pharmacologically acceptable solvent or carrier. A pharmacologically acceptable solvent or carrier may present a filler, a diluent (solvent) or their mixture. "Therapeutically justified" amount of a compound is amount of a compound of Structure (I) that causes desired biological or medical response in a patient treated by a doctor or a veterinarian. "Prophylactically justified" amount of a compound is amount of a compound of Structure (I) that prevents or suppresses the disease, or relieves progress of the disease in a patient suffering from a medical state that is tried to be prevented, suppressed or relieved by a doctor or a veterinarian.

A patient is a human in one of the aspects of the present invention.

"Eye pathologies" comprise but are not limited by: different forms of macular degeneration (MD) and other related symptoms, namely: atrophic (dry) MD, exudative (wet) MD, age-related macular retinopathy (ARM), choroidal neovascularization, detached pigment retinal epithelium (PED), atrophy of pigment retinal epithelium (RPE). The term "macular degeneration (MD)" also comprises all eye diseases irrelevant to age-related changes in a human organism, namely: vitelliform degeneration of Best, Stargardt disease, juvenile macular dystrophy, Behr's disease, Sorsby's dystrophy, Doyne honeycomb retinal dystrophy. "Symptoms related to macular degeneration" comprise but are not limited by: drusen surrounded by white-yellow spots, submacular discoid scar of tissues, choroidal neovascularization, detached pigment retinal epithelium (PED), atrophy of pigment retinal epithelium (RPE), anomalous expansion of choroidal blood vessels, blurred or disturbed vision area, central dead point, pigment anomalies, mixed layer of thin granulation located on the inner side of Bruch's membrane, thickening and lowered permeability of Bruch's membrane.

Said compositions are particularly useful for treatment and/or prophylaxis of such disorders as: cataract including senile cataract, diabetic cataract, retinopathy, detached retina, pathology of retinal vessels, eye vascular envelope, optic nerve including atrophy of optic nerve, central and peripheral chorioretinal dystrophies, in particular, uveitis; intraocular hemorrhage, traumatic hemorrhage; conjunctivitis; ophthalmic ulcer; keratitis including filamentary keratitis; glaucoma.

The reasons causing macular degeneration include but are not limited by: genetic or physical trauma, diseases such as diabetes, or infections, in particular, bacterial.

The compounds of structure (I) can be applied to efficient prophylaxis and therapy of all forms of macular degeneration (MD) and other MD related syndromes or symptoms irrespective of the reasons which have caused them.

Application of the pharmaceutical compositions of the present invention can be both somatic and local. Administration methods comprise enteral such as oral, sublingual and rectal; local such as through-dermal, intradermal and oculodermal; and parenteral. Acceptable parenteral methods of administration comprise injections, for example, intravenous, intramuscular, hypodermic injections et cetera, and noninjection methods such as intravaginal and nasal. Per ocular or per oral administration of the compounds and the pharmaceutical compositions of the present invention is more preferable. In particular, the administration can be carried out in the form of eye drops or tablets, granules, capsules or other pressed or compressed form.

When a compound of structure (I) is administered as a pharmaceutical composition, the compound of structure (I) should be mixed according to formula with a suitable amount of pharmacologically acceptable solvent or carrier so that to have the appropriate form for administration to a patient. The term "solvent" relates to diluent, auxiliary medicinal substance, filler or carrier which is mixed with the compound of structure (I) for administration to a patient. Liquors like water, and oils including petrolic, animal, vegetative and synthetic such as peanut oil, soybean oil, mineral oil and other similar oils can be used as said pharmacological carriers. Normal saline solution, acacia pitch, gelatin, starch, talc, keratin, colloid silver, urea etc can serve as said pharmacological solvents.

Said composition can also include auxiliary substances, stabilizers, thickeners, lubricant and coloring agents.

The compounds and compositions of the present invention can be administered in the form of capsules, tablets, pills, pillets, granules, syrups, elixirs, solutions, ophthalmologic solutions, suspensions, emulsions, suppositories or retarded release substances, or in any other form suitable for administration to a patient.

One of the aspects of the present invention is application of the compounds of structure (I) and compositions in the form of solutions for per oral and per ocular administration.

Therapeutically justified amount of a compound of Structure (I) required for treatment of a specific disease or symptom, depends on the nature of disease or symptom and a method of administration and should be determined at consultation with a physician in charge. In principle, upon per oral administration, acceptable doses are from 1 to 500 μg/kg of a patient body weight, 25 μg/kg of a patient body weight is more preferable, and 125 μg/kg of a patient body weight is the most preferable.

Example of Pharmaceutically Acceptable Composition in the Form of Solution for Per Oral Administration 10 mM sodium phosphate buffer, pH 6.0
SkQ1 at concentration of 125 μg/mL
Aqueous solution An Example of Pharmaceutically Acceptable Composition in the Form of Ophthalmologic Solution (Eye Drops)

10 mM sodium phosphate buffer, pH 6.5
Aqueous solution of 250 nM SkQ1
Aqueous solution of 0.9% NaCl

Figure 1:
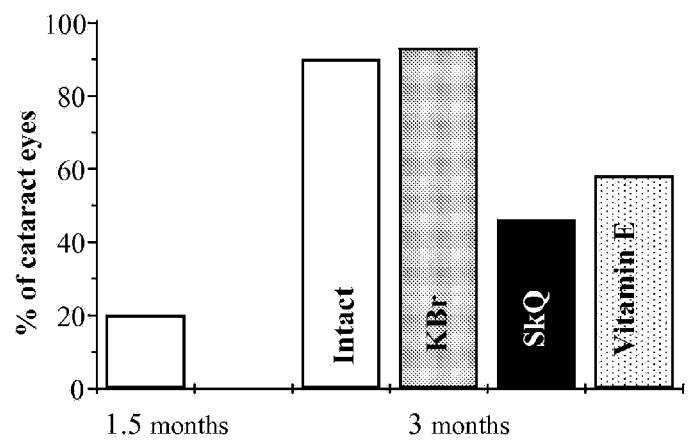
FIG. 1 shows the influence of the compounds on the cataract morbidity in OXYS rats.

The following non-limiting Examples illustrate the preparation and use of the compounds of structure I but should not be understood as limiting the invention as modifications in materials and methods will be apparent to the skilled person. The following examples should not be construed as limiting the scope of this disclosure.

EXAMPLES

1. Prophylactic Effect of SkQ1 Antioxidant of the Present Invention Against Age-Related Eye Diseases The study was carried out using OXYS and Wistar male rats. The animals were housed in cages (five rats per a cage) and kept under standard laboratory conditions (at 22±1° C., 60% relative humidity, and natural light), provided with a standard rodent diet (PK-120-1, Ltd. 'Laboratorsnab', Russia), and given water ad libitum. At the age of 1.5 months after preliminary pupil dilation with 1% tropicamide ophthalmic the rats were examined by ophthalmologist. During the period from 1.5 to 3 months, which is critical for the development of pronounced changes in eye organ of OXYS rats, the animals were given either SkQ1 (50 nmol per kg of body weight), or KBr (50 nmol per kg of body weight) or vitamin E (alfa-tocopherol acetate, 20 mg per kg). We use Vitamin E for a comparison with test antioxidants. Animals received the compounds on a small piece of dried bread before a regular meal, and the control group of animals received the same piece of bread without any compound. After completing the course of antioxidants the animals were weighed and retested with ophthalmoscope. To avoid human factor in the evaluation of compound effects, the researcher who conducted the ophthalmoscopic examination was not told which of the animals received antioxidants.

The ophthalmoscopic examination was carried out using direct ophthalmoscope "Betta", Germany. In selected animals under fluorotane narcosis (1-1.5 minutes) eyeground was photographed, fluorescent angiography with the use of "Opton" fundus-camera was conducted or crystalline lenses were examined by means of slitlamp "Opton SL30" using system of automatic image registration (biomicroscopic research).

The lens state was evaluated according to the classification system accepted in clinical practice (L. A. Katsnelson, T. I. Forofonova, A. Ya. Bunin, 1990) with grades ranging from 0 to 3: score 0—the lens is clear; score 1—spotted weak cloudiness; score 2—multiple spots of cloudiness and score 3—intense cloudiness of the lens core and nucleus. The presence and the degree of spotted changes in macular area were evaluated according to accepted classification: score 0—no changes; score 1—the $1^{st}$ stage of pathology, when small yellow deposits, known as "drusen" appear underneath the macula; score 2—$2^{nd}$ stage, the development of prominent yellow spot with sharp edges with the size of 0.5 to 1 of the disk diameter (exudative detachment of pigment retinal epithelium); and score 3—$3^{rd}$ stage with extensive hemorrhage into macular area.

Statistical processing of the results was carried out using the factorial dispersive analysis (ANOVA/MANOVA, Statistica, 5) with post hoc comparison of group average (Newman-Keul test) considering genotype and preparation as independent factors.

Results Obtained

Ophthalmoscopic examination did not reveal any changes in the lenses or in the macular area of the retina in 1.5 and 3 month-old Wistar rats. In contrast, in OXYS rats early cataract (score 1) was observed in 20% of cases (FIG. 1) and macular degeneration of the $1^{st}$ stage —in 10% of cases at the age of 1.5-months (FIG. 2).

At the age of 3 months in the control intact group of OXYS rats pathological changes of lenses were observed in 90% of examined eyes, including 35% of eyes with $2^{nd}$ stage of cataract, with ring-shaped and nuclear cataracts prevailed (FIG. 1).

Figure 2:
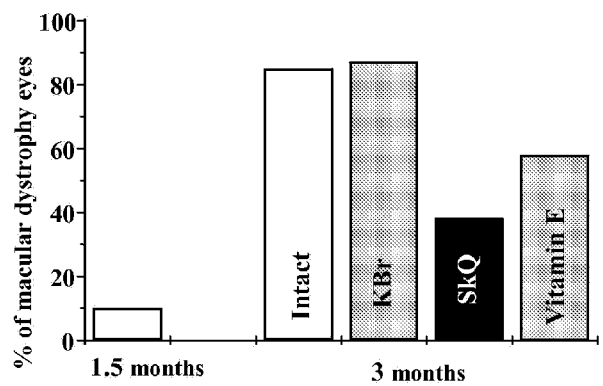
FIG. 2 demonstrates the influence of the compounds on the macular dystrophy morbidity in OXYS rats.

Macular dystrophy was observed in 85% of eyes from control group of animals of which 16% corresponded to the $2^{nd}$ stage of this pathology (FIG. 2). In the group of OXYS rats supplemented with KBr, lens changes were observed in 93% of eyes, with 57% of total number of eyes having $2^{nd}$ stage of cataract progression. Changes in the macular area of the retina were observed in 87% of eyes of animals from this group and 13% of these changes corresponded to the $2^{nd}$ stage of the disease. Taking into account that cataract already affected 20% of eyes, 73% of rat eyes have been newly affected, and respectively macular dystrophy has affected 77% of eyes.

In animals supplemented with SkQ1 (FIG. 1) some lens changes were registered in 46% of cases, however these changes corresponded to the $1^{st}$ stage of cataract. Changes in the macular area of the retina in OXYS rats of this group were revealed in 38% of cases and also were defined as the $1^{st}$ stage of macular degeneration (FIG. 2). Of this group of rats supplemented with SkQ1, cataract was revealed in 26% of cases (2.8 times less than in the group of rats supplemented with KBr), macular dystrophy was detected in 28% of cases (also 2.8 times less than in the control group).

Figure 3:
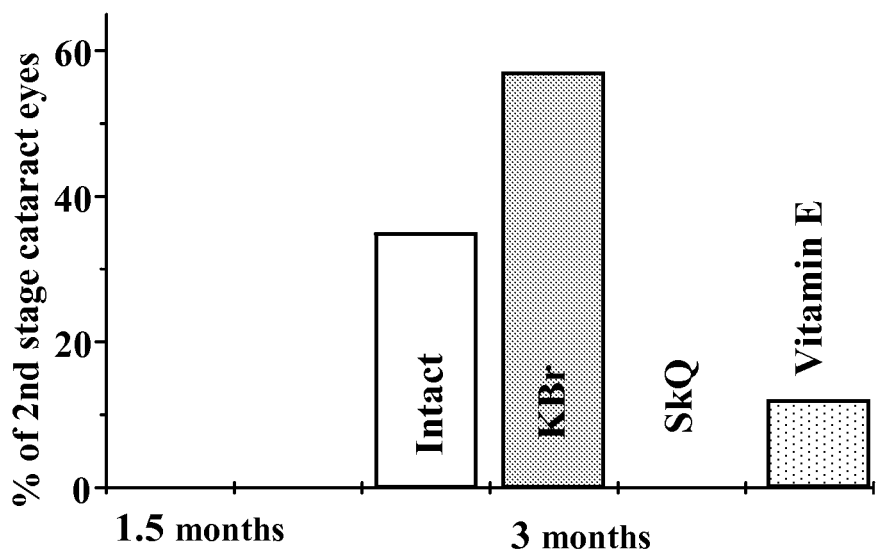
FIG. 3 shows the influence of the compound on the cataract progression in OXYS rats.
Figure 4:
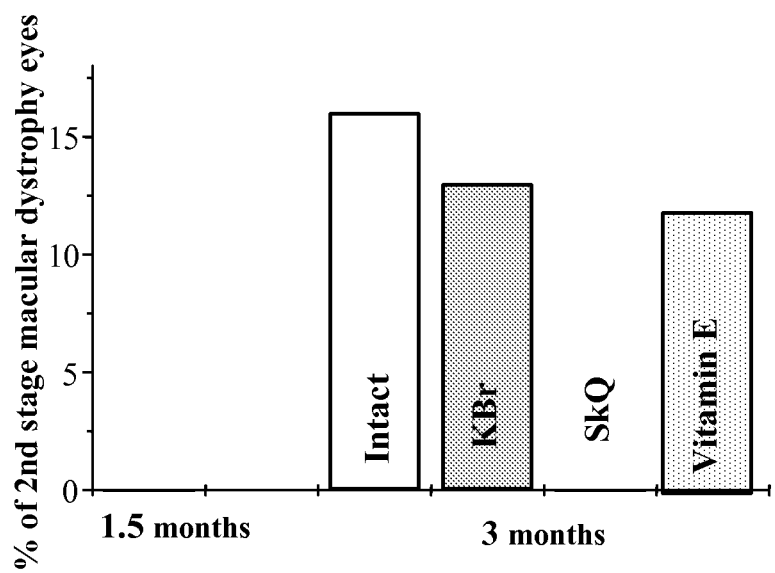
FIG. 4 shows the influence of the compound on the macular degeneration progression in OXYS rats.
Figure 5:
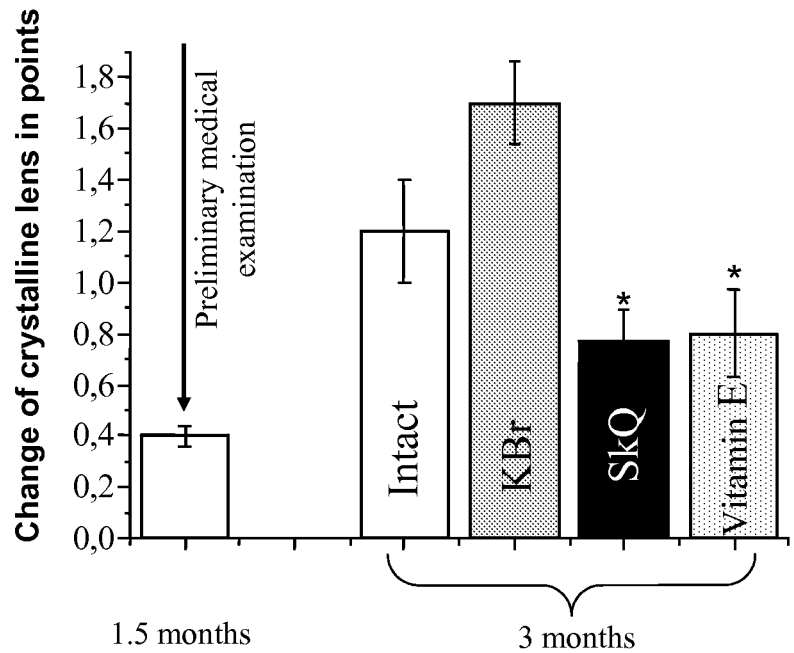
FIG. 5 compares the state of crystalline lens of OXYS rats before administering and after 45-day course of KBr, SkQ1 or vitamin E.
Figure 6:
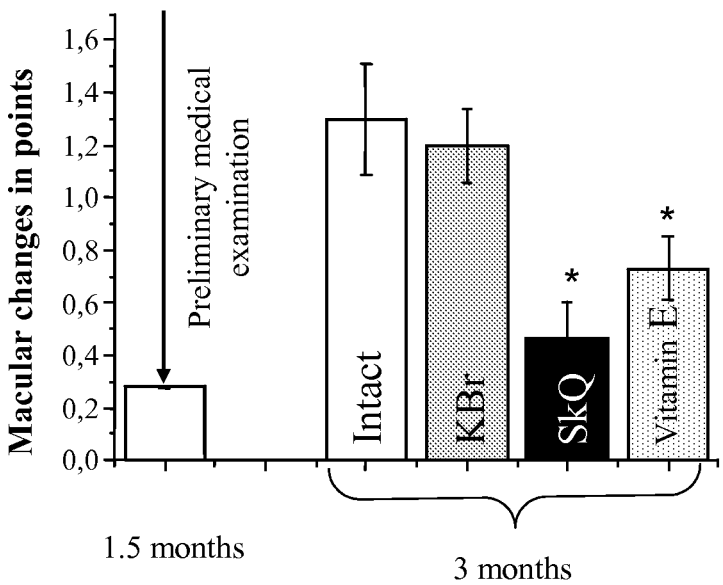
FIG. 6 shows degenerative changes in macular region of retina of OXYS rats before administering and after 45-day course of KBr, SkQ1 and vitamin E.

In the group of rats supplemented with vitamin E, lens changes were registered in 58% of cases (38% has been added, 1.8 times less than in the control intact group), with 12% of changes corresponding to the $2^{nd}$ stage of the cataract. Changes in the macular area of the retina were revealed in 54% of OXYS rats from this group (1.5 times less than in the control intact group), including 8% corresponding to the $2^{nd}$ stage of macular degeneration. Administration of SkQ1 not only decreased the cataract and macular dystrophy morbidity but also essentially affected their progression (see FIG. 3 and FIG. 4 respectively).

It is remarkable that in one month after the end of the course of SkQ1 administration, no any changes in the state of retina and crystalline lens of the rats supplemented with SkQ1 have been observed, in contrast to the control group of animals.

Thus, the investigations performed prove the efficiency of SkQ1 application for prophylaxis of age-related eye diseases including prophylaxis of cataract and macular dystrophy—the main age-related eye pathologies in elders.

2. Therapeutic Effect of SkQ1 Antioxidant of the Present Invention Against Age-Related Eye Diseases The experiment followed the same pattern as said investigation demonstrating prophylactic effect of SkQ1 except that in this experiment OXYS and Wistar rats at the age of 10.5 months were used.

Results

Table 1 shows the results of examination of animals before administering at the age of 10.5 months and after the therapy course. In Wistar rats, changes of crystalline lenses and retina exceeding characteristic parameters for the appropriate age were revealed that is due to specific conditions of cage keeping of these animals. Examination of Wistar rats in 45 days did not reveal any changes in the state of crystalline lenses, the compounds also did not affect substantially the state of lenses. Among Wistar rats supplemented with SkQ1, animals with changes of retina which could be qualified as appropriate to even the most initial stage of disease were practically absent.

Figure 7:
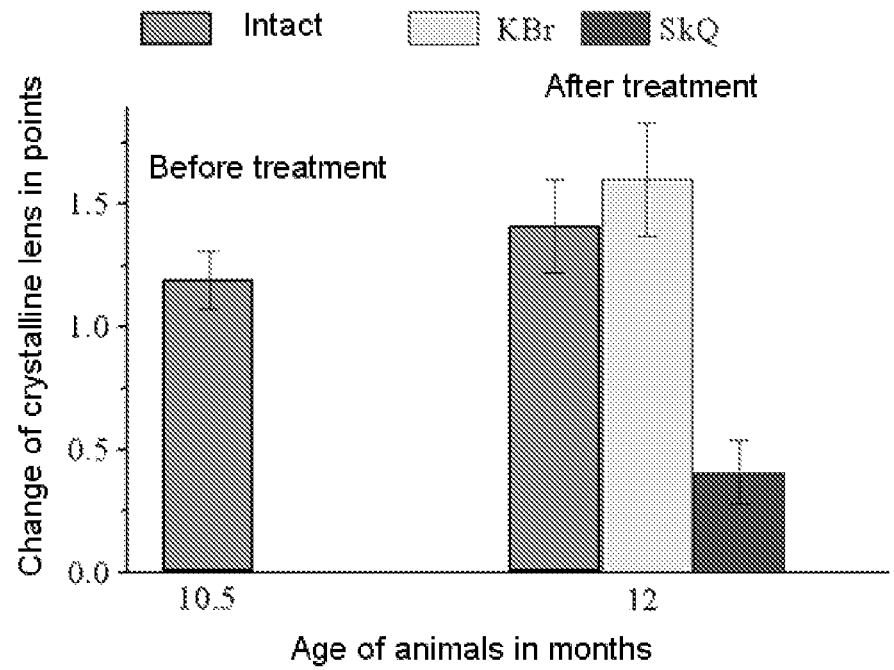
FIG. 7 demonstrates the therapeutic effect of SkQ1 on the state of crystalline lens of OXYS rats.
Figure 8:
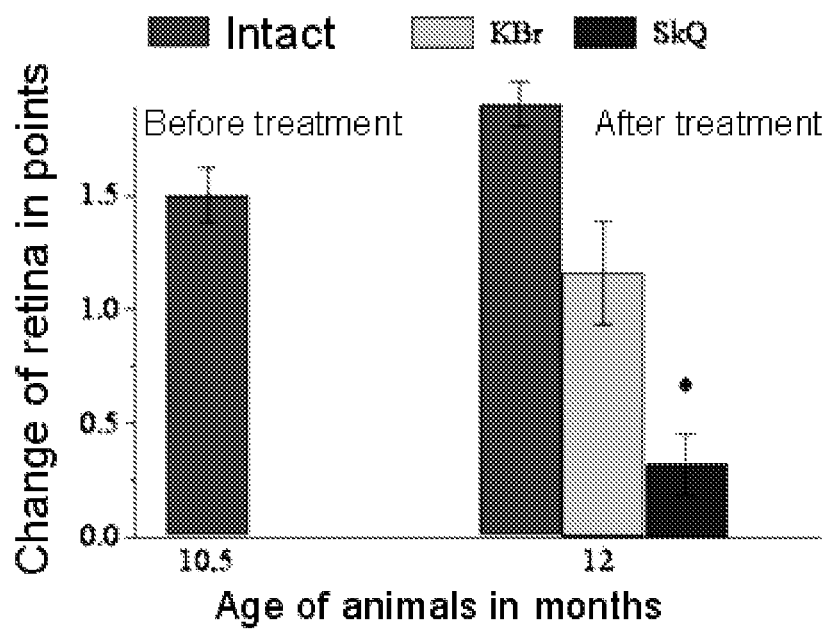
FIG. 8 demonstrates the therapeutic effect of SkQ1 on the state of retina of OXYS rats.

Pair comparisons showed that in the control intact group of OXYS rats, pathological changes of lenses and retina for 1.5 months have authentically aggravated (p<0.04 and p<0.01 accordingly). In animals supplemented with KBr, changes of lenses have authentically aggravated whereas no any changes of retina have been observed. It should be emphasized that the state of eyes before and after the therapy course has been compared therefore when the average values are compared (Table 1, FIGS. 7 and 8), in OXYS rats supplemented with SkQ1 these pathological changes have really been much less pronounced. In retina of this group of animals, significant reduction of puffiness was observed; there was also reduction of quantity and area of ischemic centers, resolution of hemorrhages.

TABLE 1

| | Preliminary examination at the age of 10.5 months | Examination after therapy course at the age of 12 months | | |
| --- | --- | --- | --- | --- |
| | | Intact | KBr | SkQ1 |
| | | OXYS | | |
| Macular | 1.46 ± 1.18 | 1.90 ± 0.10 | 1.13 ± 0.17 | 0.32 ± 0.13 |
| Lenses | 1.19 ± 0.12 | 1.41 ± 0.19 | 1.6 ± 0.23 | 0.41 ± 0.13 |
| | | Wistar | | |
| Macular | 0.48 ± 0.19 | 0.5 ± 0.25 | 0.25 ± 0.10 | 0.09 ± 0.06 |
| Lenses | 0.40 ± 0.23 | 0.5 ± 0.22 | 0.5 ± 0.15 | 0.54 ± 0.14 |

The state of animal eyes before and after course of SkQl (50 nmol per kg of body weight). Changes of lenses and macular area of retina are given with grades (score).

The data obtained proves the therapeutic effect of SkQ1-based pharmaceutical composition on animals suffering from cataract or retinopathy corresponding to macular dystrophy of retina in humans.

The invention claimed is:

1. An ophthalmologic solution comprising:
NaCl; and
a therapeutically effective amount of a compound of Structure (I):

(I)

wherein:
A is an effector—antioxidant of structure:

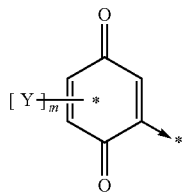

and/or reduced form thereof, wherein:
   m=2; and
   Y is methyl;
L is a linker group, comprising:
   a) a straight or branched hydrocarbon chain which can be optionally substituted by one or more substituents and optionally contains one or more double or triple bonds; or
   b) a natural isoprene chain;
n is an integer from 1 to 20; and
B is a targeting group, comprising $Sk^+Z^-$, wherein:
   Sk is a lipophilic cation; and
   Z is a pharmacologically acceptable anion; and
a pharmaceutically acceptable carrier thereof.

2. The solution of claim 1, wherein the compound of Structure (I) is SkQ1:

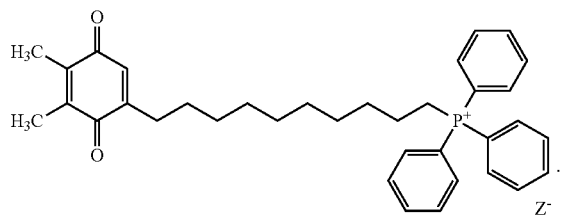

3. The solution of claim 1, wherein NaCl is present at 0.9%.

4. The solution of claim 1, further comprising sodium phosphate buffer with pH 6.5.

5. The solution of claim 4, wherein the sodium phosphate buffer is present at 10 mM.

6. The solution of claim 1, wherein the compound of Structure (I) is SkQ1 which is present at 250 nM.

7. The solution of claim 4, wherein:
   the compound of Structure (I) is SkQ1 which is present at 250 nM;
   the sodium phosphate buffer is 10 mM, pH 6.5; and
   the NaCl is present at 0.9%.

* * * * *